United States Patent [19]
Rehmann

[11] Patent Number: 6,006,668
[45] Date of Patent: Dec. 28, 1999

[54] GLOSSY OR MATTE-FINISH MEDIA DETECTOR AND METHOD FOR USE IN A PRINTING DEVICE

[75] Inventor: David A. Rehmann, Vancouver, Wash.

[73] Assignee: Hewlett-Packard Company, Palo Alto, Calif.

[21] Appl. No.: 09/063,344

[22] Filed: Apr. 20, 1998

[51] Int. Cl.[6] .................. G01N 21/17; G01N 21/21; G01N 21/47; B41J 29/00
[52] U.S. Cl. .................. 101/484; 400/703; 250/225; 250/559.16; 356/369
[58] Field of Search .................. 250/559.16, 559.17, 250/225; 356/369; 400/703; 101/484

[56] References Cited

U.S. PATENT DOCUMENTS

| | | | |
|---|---|---|---|
| 2,947,212 | 8/1960 | Woods | 356/369 |
| 3,105,908 | 10/1963 | Burkhardt et al. | 250/372 |
| 3,667,038 | 5/1972 | Cutler et al. | 324/77 R |
| 4,617,580 | 10/1986 | Miyakawa | 346/136 |
| 4,945,253 | 7/1990 | Frohardt | 250/559.16 |
| 4,990,790 | 2/1991 | Yoshihara | 356/369 |
| 5,028,138 | 7/1991 | Wolff | 356/369 |
| 5,055,892 | 10/1991 | Gardner et al. | 357/17 |
| 5,101,393 | 3/1992 | Marshall | 369/44.37 |
| 5,162,660 | 11/1992 | Popil | 250/559.01 |
| 5,387,976 | 2/1995 | Lesniak | 356/379 |
| 5,572,314 | 11/1996 | Hyman, Jr. et al. | 356/128 |
| 5,699,163 | 12/1997 | Todoroki et al. | 356/369 |
| 5,774,146 | 6/1998 | Mizutani | 347/43 |
| 5,925,889 | 7/1999 | Guillory et al. | 250/559.16 |

FOREIGN PATENT DOCUMENTS

| | | | |
|---|---|---|---|
| 53-23678 | 3/1978 | Japan | 356/369 |
| 57-172235 | 10/1982 | Japan . | |
| 02196944 | 8/1990 | Japan . | |
| 1383166 | 3/1988 | U.S.S.R. | 356/369 |

OTHER PUBLICATIONS

Patent Abstract of Japan, Publication Number 05264441; Published on Oct. 12, 1993; Niigata Denki KK.
Patent Abstract of Japan, Publication Number 08297022; Published on Nov. 12, 1996;Mitsubishi Electric Corp.
Patent Abstract of Japan, Publication Number 08159957; Published on Jun. 21, 1996, Chino Corp.

*Primary Examiner*—John Hilten
*Assistant Examiner*—Daniel J. Colilla
*Attorney, Agent, or Firm*—Erik A. Anderson

[57] ABSTRACT

A media detector for use in a printing device and method of differentiating between glossy-finish and matte-finish print media are disclosed. An embodiment of the media detector includes a source, sensor, and polarized filter. The source transmits an unpolarized first light signal and is positioned so that this signal is transmitted toward a sheet of print media at a first angle with respect to a normal to a surface of the sheet of print media. The sensor is positioned to detect an intensity of a reflected light signal from the sheet of print media. The polarized filter is positioned between the sensor and the sheet of print media so that the intensity of the reflected light signal detected by the sensor is less for a polarized reflected light signal than for an unpolarized reflected light signal. Polarization of the reflected light signal is dependent upon the first angle. A method in accordance with the present invention transmits an unpolarized first light signal toward a sheet of print media at a first angle with respect to a normal to a surface of the sheet of print media. This method also detects an intensity of a reflected light signal from the sheet of print media and differentiates between a polarized reflected light signal and unpolarized reflected light signal to determine whether the sheet of print media has a glossy-finish or a matte-finish. Other characteristics and features of the above-described media detector and method are described herein, as are alternative embodiments.

15 Claims, 6 Drawing Sheets

GLOSSY OR MATTE-FINISH MEDIA DETECTOR AND METHOD FOR USE IN A PRINTING DEVICE

BACKGROUND AND SUMMARY

The present invention relates to printing devices. More particularly, the present invention relates to a media detector for and a method of differentiating between glossy-finish and matte-finish print media.

Printing devices, such as inkjet printers, use printing composition (e.g., ink or toner) to print text, graphics, images, etc. onto print media. The print media may be of any of a variety of different types. For example, the print media may include letter quality paper, transparencies, envelopes, photographic print stock, cloth, etc. These print media may be placed in one of two broad categories relating to the finish of the surface of the print medium. These categories are glossy-finish for things such as transparencies and photographic print stock and matte-finish for things such as letter quality paper and envelopes. A glossy-finish is specifically defined herein as a print media finish that provides a surface brightness or shine when illuminated by a light source. A matte-finish is specifically defined herein as a print media finish that lacks surface brightness or shine when illuminated by a light source. Glossy-finish and matte-finish print media each have various characteristics that ideally should be accounted for during printing, otherwise a less than optimal printed output may occur.

One way in which a printing device can be configured to a particular to print media is to have a user make manual adjustments to the printing device based upon these characteristics. One problem with this approach is that it requires user intervention which is undesirable. Another problem with this approach is that it requires a user to correctly identify and differentiate between glossy-finish and matte-finish print media which some users may be unable to do. A further problem with this approach is that a user may incorrectly manually configure the printing device so that optimal printing still does not occur in spite of user intervention.

A device and method that automatically differentiates between gloss-finish and matte-finish print media would be a welcome improvement. Accordingly, the present invention is directed to alleviating these above-described problems and achieving this end.

An embodiment of a media detector in accordance with the present invention for use in a printing device includes a source, a sensor, and a polarized filter. The source transmits an unpolarized first light signal and is positioned in the printing device so that the first light signal is transmitted toward a sheet of print media in the printing device at a first angle with respect to a normal to a surface of the sheet of print media. The sensor is positioned in the printing device to detect an intensity of a reflected light signal from the sheet of print media. The polarized filter is positioned between the sensor and the sheet of print media so that the intensity of the second light signal detected by the sensor is less for a polarized reflected light signal than for an unpolarized reflected light signal. Polarization of the second light signal is dependent upon the first angle.

The above-described media detector may be modified and include the following characteristics described below. The first angle may be selected such that the reflected light signal is polarized in a plane substantially orthogonal to a polarization of the polarized filter. The media detector may further include a second sensor and a second polarized filter. In this case, the second sensor is positioned in the printing device to detect the intensity of the reflected light signal from the sheet of print media. The second polarized filter is positioned between the second sensor and the sheet of print media, and oriented so that the polarization of the second polarized filter is substantially parallel to a polarization of the reflected light signal.

The reflected light signal may be polarized for a glossy-finish sheet of print media and unpolarized for a matte-finish sheet of print media. The media detector may be in a printing device. The first angle may be selected to be substantially equal to a Brewster's angle.

An alternative embodiment of a media detector in accordance with the present invention also includes a source, a sensor, and a polarized filter. In this embodiment, the source transmits an unpolarized first light signal in a first direction and the sensor is configured to detect an intensity of a reflected light signal having a second direction different than the first direction. The polarized filter is positioned between the sensor and a sheet of print media, and oriented so that the polarization of the polarized filter is substantially perpendicular to a polarization of the reflected light signal. Polarization of the reflected light signal is dependent upon the first direction of the first light signal.

The above-described alternative embodiment of the media detector may be modified and include the following characteristics described below. The media detector may further include a second sensor and second polarized filter. The second sensor is positioned in the printing device to detect the intensity of the reflected light signal from the sheet of print media. The second polarized filter is positioned between the second sensor and the sheet of print media, and oriented so that polarization of the second polarized filter is substantially parallel to the polarization of the reflected light signal.

The reflected light signal may be polarized for a glossy-finish sheet of print media and unpolarized for a matte-finish sheet of print media. The first direction may be selected to polarize the reflected light signal in a plane substantially orthogonal to a polarization plane of the polarized filter. The media detector may be in a printing device.

Another alternative embodiment of a media detector in accordance with the present invention for use in a printing device includes structure for producing a unpolarized first light signal and structure for sensing polarization of a reflected light signal from a sheet of print media in response to the first light signal so that the printing device can differentiate between a glossy-finish sheet of print media and a matte-finish sheet of print media to help optimize printing by the printing device. This alternative embodiment of a media detector for use in a printing device may include the following characteristics described below.

The reflected light signal may be polarized for glossy-finish print media and unpolarized for matte-finish print media.

The structure for sensing may include a sensor and polarized filter. In this case, the sensor is positioned in the printing device to detect an intensity of the reflected light signal from the sheet of print media. The polarized filter is positioned between the sensor and the sheet of print media so that the intensity of the reflected light signal detected by the sensor is less for a polarized reflected light signal than for an unpolarized reflected light signal. This embodiment of the media detector may also include a second sensor and a second polarized filter. In such cases, the second sensor is positioned in the printing device to detect the intensity of the reflected light signal from the sheet of print media. The second polarized filter is positioned between the second sensor and the sheet of print media, and oriented so that the polarization of the second polarized filter is substantially parallel to the polarization of the reflected light signal.

This alternative embodiment of a media detector may be in a printing device.

A method of differentiating between glossy-finish and matte-finish print media in accordance with the present invention for use in a printing device includes the step of transmitting an unpolarized first light signal toward a sheet of print media at a first angle with the respect to a normal to a surface of the sheet of print media. The method additionally includes the step of detecting an intensity of a reflected light signal from the sheet of print media. The method further includes the step of differentiating between a polarized reflected light signal and an unpolarized light signal to determine whether the sheet of print media has a glossy-finish or a matte-finish.

The above-described method may include the following additional steps described below. The method may include the additional step of selecting the first angle such that the reflected light signal is polarized in a plane substantially orthogonal to a plane including the normal. The method may include the step of selecting the first angle to be substantially equal to a Brewster's angle.

Other objects, advantages, and novel features of the present invention will become apparent from the following detailed description of the invention when considered in conjunction with the accompanying drawings.

DETAILED DESCRIPTION OF THE DRAWINGS

Figure 1:
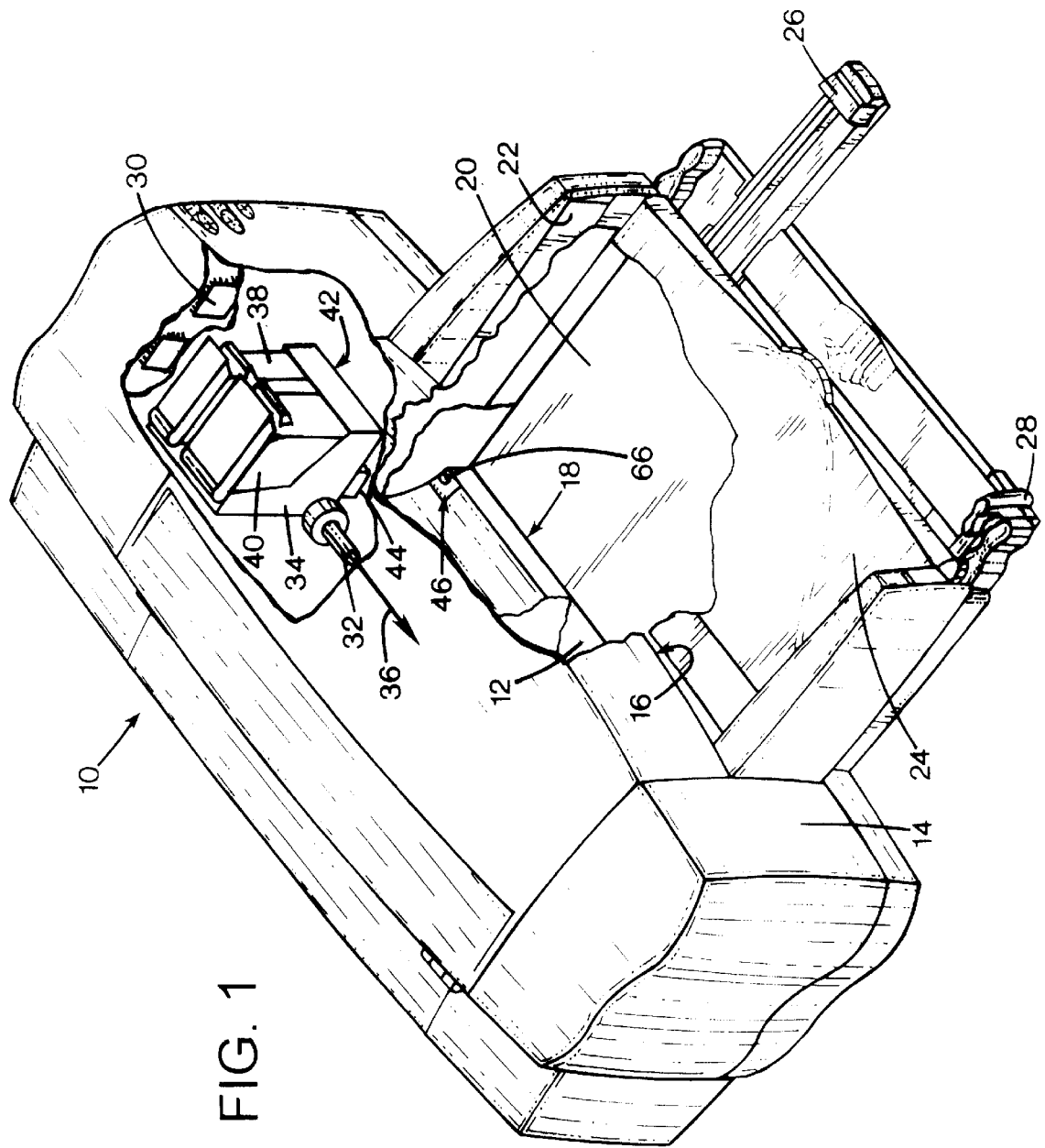
FIG. 1 is a perspective view of a printing device that includes an embodiment of a media detector in accordance with the present invention.

FIG. 1 illustrates an embodiment of a printing device, here shown as an inkjet printer 10, which may be used for printing business reports, correspondence, desktop publishing, and the like, in an industrial, office, home or other environment. A variety of inkjet printing devices are commercially available. For instance, some of the printing devices that may embody the present invention, described below, include plotters, portable printing units, copiers, cameras, video printers, laser printers, and facsimile machines, to name a few. For convenience, the concepts of the present invention are illustrated in the environment of inkjet printer 10. It is to be understood, however, that the present invention may be used in other printing devices as well, such as those described above.

While it is apparent that printing device components may vary from model to model, a typical inkjet printer 10 includes a chassis 12 surrounded by a housing or casing enclosure 14, typically made of a plastic material. Sheets of print media (not shown FIG. 1) are fed through a print zone 16 by a print media handling system 18. The print media may be any type of suitable sheet material, such as letter quality paper, card stock, envelopes, photographic print stock, transparencies, and cloth. Print media handling system 18 has a feed tray 20 for storing sheets of print media before printing. A series of conventional motor-driven print media drive rollers (not shown in FIG. 1) may be used to move the print media from tray 20 into print zone 16 for printing. After printing, the sheet then lands on a pair of retractable output drying wing members 22, only one of which is shown in FIG. 1, in a retracted position. Wings 22 momentarily hold the newly printed sheet above any previously printed sheets still drying in output tray portion 24 before pivotally retracting to the sides to drop the newly printed sheet into output tray 24. Print media handling system 18 may include a series of adjustment mechanisms for accommodating different sizes of print media, including letter, legal, A-4, envelopes, etc., such as a sliding length adjustment lever 26, and a sliding width adjustment lever 28.

Printing device 10 also has a printer controller, illustrated schematically as a microprocessor 30, that receives instructions from a host device, typically a computer, such as a personal computer (not shown). Many of the printer controller functions may be performed by the host computer, by electronics on board the printer, or by interactions between the two. A monitor (not shown) coupled to the computer host may be used to display visual information to an operator, such as the printer status or a particular program being run on the host computer. Personal computers, their input devices, such as a keyboard and/or a mouse, and monitors are well known to those skilled at the art.

A carriage guide rod 32 is supported by chassis 12 to slideably support an inkjet carriage 34 for travel back and forth across print zone 16 along a scanning access 36 defined by guide rod 32. A conventional carriage propulsion system (not shown) may be used to drive carriage 34. This conventional carriage propulsion system includes a positional feedback system which communicates carriage position signals to controller 30. An example of such a carriage propulsion system is a carriage drive gear and DC motor assembly that is coupled to drive an endless belt secured in a conventional manner to carriage 34, with the motor operating in response to controls signals received from printer controller 30. To provide carriage positional feedback information to printer controller 30, an optical encoder reader may be mounted to carriage 34 to read an encoder strip extending along the path of carriage travel.

In print zone 16, the print media sheet receives ink from an ink cartridge, such as black ink cartridge 38 and/or color ink cartridge 40 which are parts of the printing mechanism of printing device 10. Cartridges 38 and 40 are often called "pens" by those skilled in the art. The illustrated color pen 40 is a tri-color pen, although in some embodiments, a set of discreet monochrome pens may be used.

The illustrated pens 38 and 40 each include reservoirs for storing a supply of ink. Pens 38 and 40 have printheads 42 and 44, respectively, each of which has an orifice plate with plurality of nozzles formed therethrough in manner well known to those skilled in the art. The illustrated printheads 42 and 44 are thermal inkjet printheads, although other types of printheads may be used, such as piezoelectric printheads. Printheads 42 and 44 typically include a substrate layer having a plurality of resistors which are associated with the nozzles. Upon energizing a selected resistor, a bubble of gas is formed to eject a droplet of ink from the nozzle onto print media in print zone 16. The printhead resistors are selectively energized in response to enabling or firing command control signals, which may be delivered by a conventional multi-conductor strip (not shown) from controller 30 to printhead carriage 34, and through conventional interconnects between carriage 34 and pens 38 and 40 to printheads 42 and 44.

An embodiment of a media detector 46 constructed in accordance with the present invention is shown in FIG. 1. Media detector 46 is used for detecting whether glossy-finish or matte-finish print media is used in printing device 10 and transmitting this information to controller 30, as more fully discussed below. As used herein, glossy-finish is specifically defined as a print media finish that provides a surface brightness or shine when illuminated by a light source. As also used herein, a matte-finish is specifically defined as a print media finish that lacks surface brightness or shine when illuminated by a light source. Controller 30 is configured to utilize this information in controlling operation of the printing mechanism to help optimize printing by printing device 10, as more fully discussed below.

Figure 2:
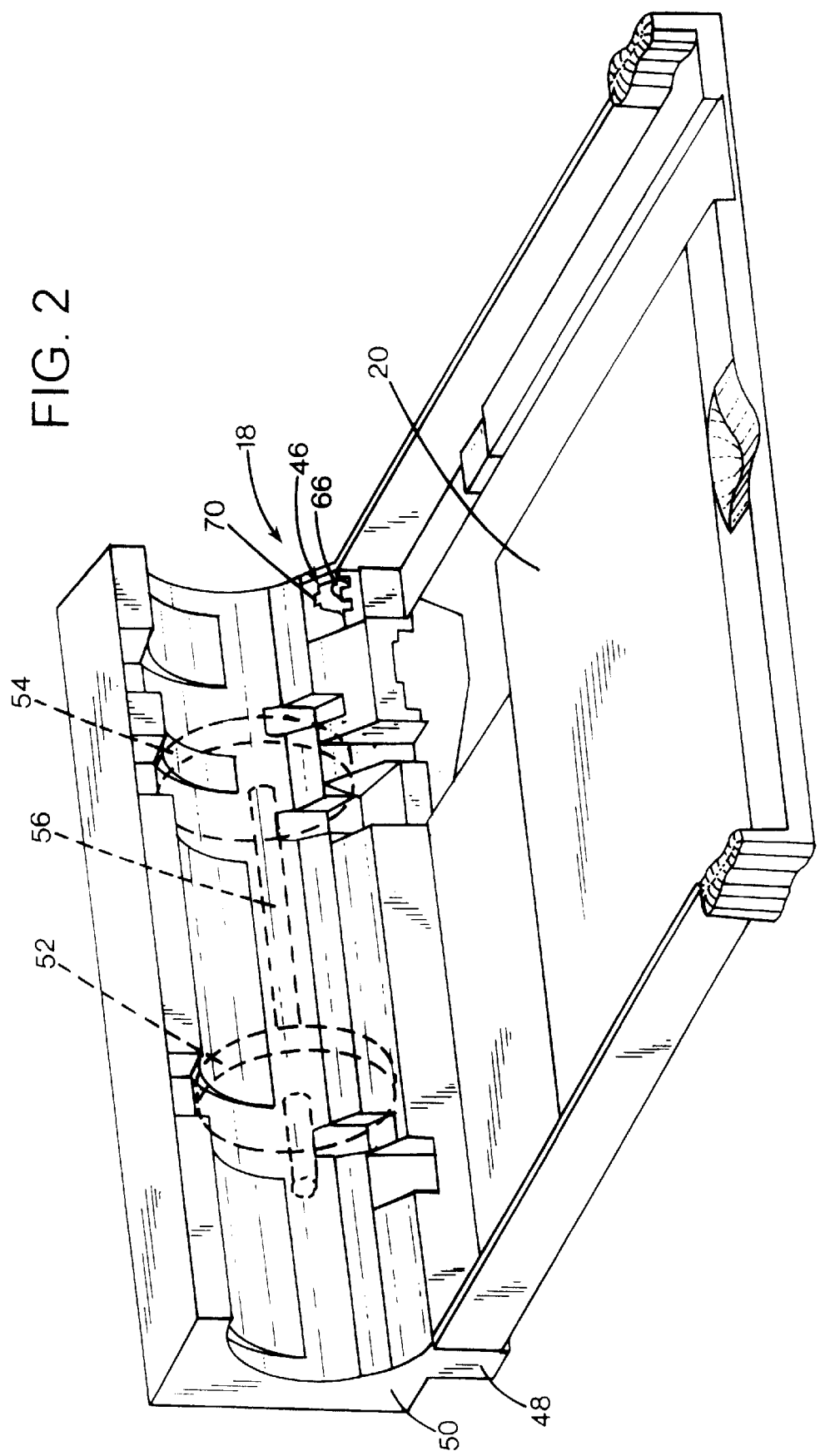
FIG. 2 is a perspective view of a print media handling system of the printing device shown in FIG. 1 and of the embodiment of the media detector of the present invention shown in FIG. 1.

A perspective view of print media handling system 18 and media detector 46 is shown in FIG. 2. As can be seen FIG. 2, print media handling system 18 includes a lower print media guide 48 and an upper print media guide 50. Print media handling system 18 also includes a pair of print media drive rollers 52 and 54 positioned adjacent lower and upper print media guides 48 and 50 and driven by a print media drive roller shaft 56. Shaft 56 is coupled to and driven by a motor, which is not shown FIG. 2.

In operation, print media drive rollers 52 and 54 select or "pick" a sheet of print media in feed tray 20 and transport the sheet of print media to print zone 16 for printing by cartridges 38 and 40 of the printing mechanism of printing device 10. During this transport, the sheet of print media moves between rollers 52 and 54 and upper and lower print media guides 48 and 50. As can be seen FIG. 2, media detector 46 of the present invention is positioned in lower print media guide 48 so that during transport of the sheet of print media to print zone 16, the sheet of print media passes over media detector 46, as more fully discussed below.

Figure 3:
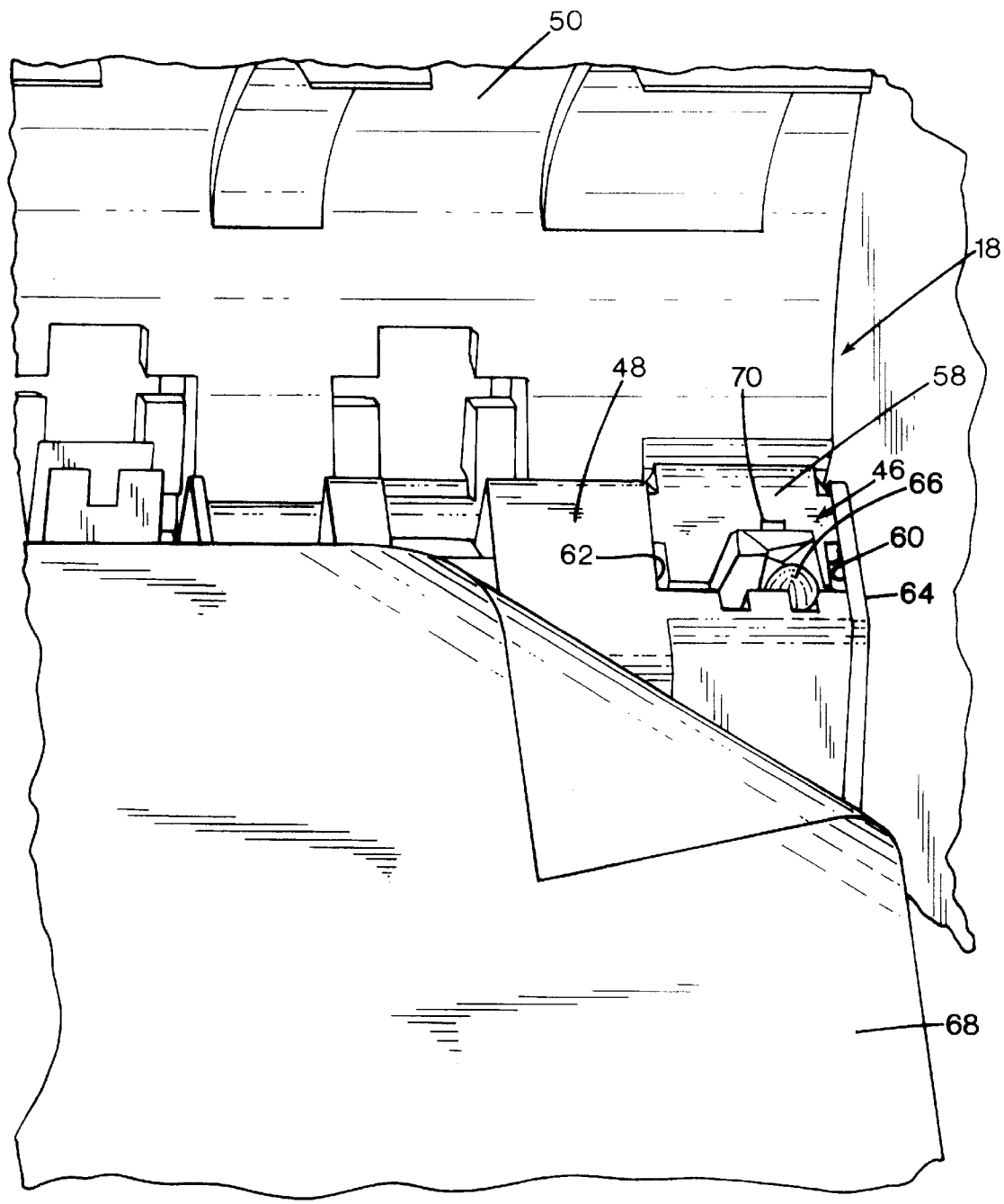
FIG. 3 is an enlarged view of the print media handling system and media detector shown FIG. 2, and of a sheet of print media moving past the media detector via the print media handling system.

An enlarged view of print media handling system 18 and media detector 46 is shown FIG. 3. Drive rollers 52 and 54 and shaft 56 of print media handling system 18 have been removed for clarity. As can be seen in FIG. 3, media detector 46 includes a housing 58 that is secured in lower print media guide 48 inside a recess 60 defined by walls 62 and 64 of lower print media guide 48. Media detector 46 may be secured within recess 60 by things such as detents on housing 58 or adhesive.

As can be seen in FIG. 3, media detector 46 includes a light emitting diode (LED) 66 that acts as a source of a first light signal that is directed at sheets of print media transported by the print media handling system 18 to print zone 16, such as sheet of print media 68 shown in FIG. 3. LED 66 emits an unpolarized light signal. This light signal may be of a single wavelength or a range of wavelengths.

Media detector 46 also includes one or two sensors (not shown in FIG. 3) and one or two polarized filters (also not shown in FIG. 3) located below opening 70 in housing 58 to detect an intensity of a reflected light signal from sheet of print media 68, as more fully discussed below.

Figure 4:
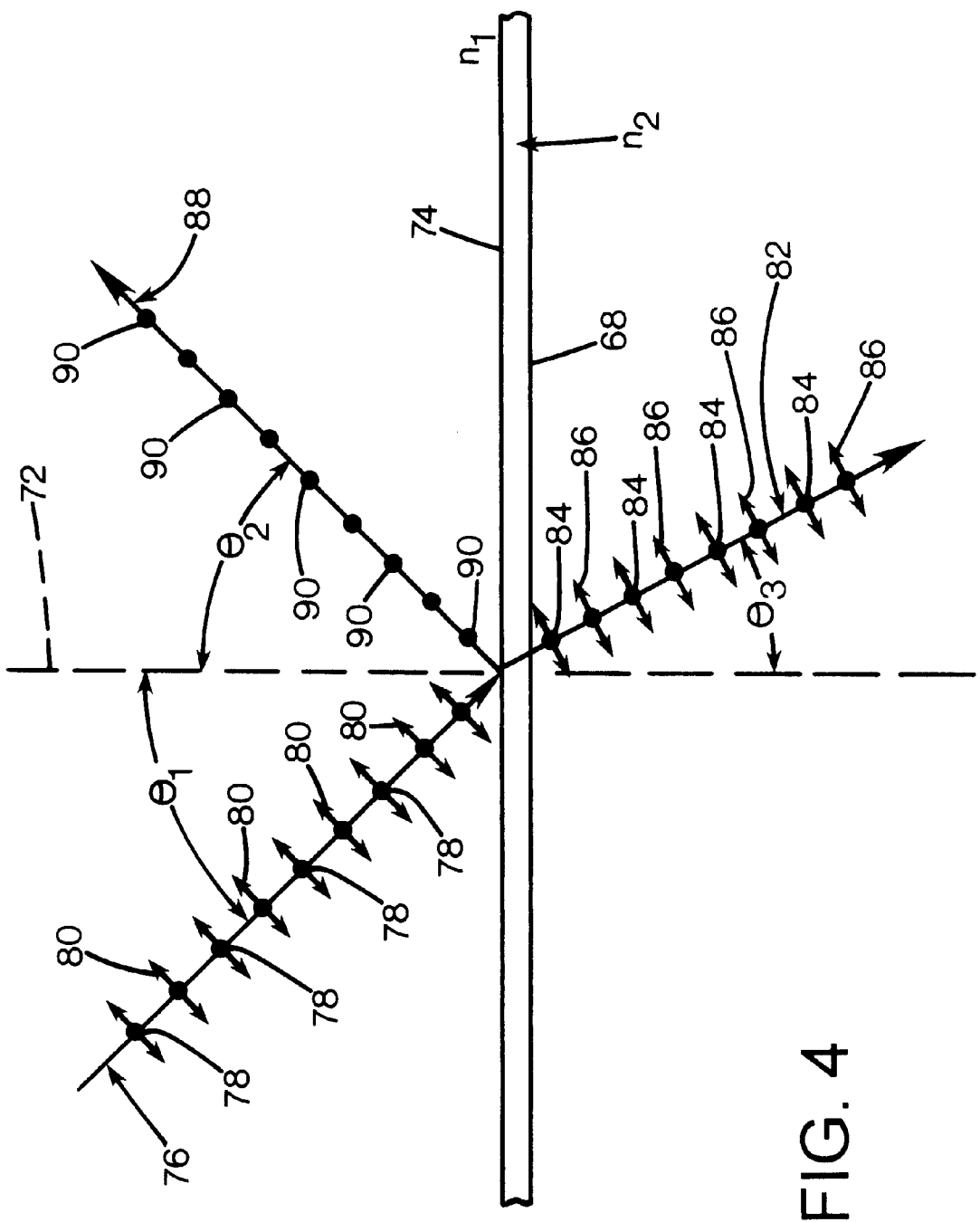
FIG. 4 is a diagram illustrating the principle of Brewster's Law which is used by the present invention.

The present invention utilizes a phenomenon known Brewster's Law to detect whether glossy-finish or matte-finish print media is at print zone 16 of printing device 10. FIG. 4 is a diagram illustrating Brewster's Law. In FIG. 4, a sheet 68 of print media is shown, as is a normal 72 to a surface 74 of print media sheet 68. In FIG. 4, air, which has an index of refraction ($n_1$) of approximately 1.00, is above print media sheet 68. Also in FIG. 4, the index of refraction of print media sheet 68 is represented by $n_2$.

An incident, unpolarized light signal 76 from LED source 66 is shown which can be resolved into two components, one perpendicular to a plane of incidence, which is defined by the plane of FIG. 4 and represented by dots 78, and one lying in this plane, represented by arrows 80. For a completely unpolarized incident light signal 76, components 78 and 80 are of substantially equal amplitude.

According to Snell's Law, incident light signal 76 will be refracted toward normal 72 as it travels from air through a non-dispersive sheet of print media, such as a transparency. This refracted light signal is illustrated in FIG. 4 by reference numeral 82. As with signal 76, signal 82 may be resolved into two components, one perpendicular to the above-described plane of incidence and represented by dots 84, and one lying in this plane, represented by arrows 86.

According Snell's Law, the index of refraction ($n_1$) multiplied by the sine of the angle of incidence ($\theta_1$) of signal 76 with respect to normal 72 is equal to the index of refraction of print media 68 ($n_2$) multiplied by the sine of the angle of refraction ($\theta_3$) of signal 82 with respect to normal 72. That is:

$$n_1 \sin \theta_1 = n_2 \sin \theta_3$$

As incident unpolarized light signal 76 passes from air through sheet 68, a certain quantity of light is reflected from surface 74 of sheet 68, as shown in FIG. 4 by reflected light signal 88. As can be seen FIG. 4, signal 88 is reflected from surface 74 of sheet 68 at an angle ($\theta_2$) with respect to normal 72. As is known by those skilled in the art, $\theta_1$ is equal to $\theta_2$. That is, signal 88 reflected from surface 74 of sheet 68 at an angle with respect to normal 72 equal to the angle of incident signal 76 with respect to normal 72.

Empirically, it can be shown that for non-dispersive material, such as transparencies and photo quality media, at a particular angle of incidence of light signal 76 with respect to normal 72, components of signal 88 that lie in the plane of incidence of FIG. 4 will be zero and only components that are perpendicular to the plane of incidence will remain, as represented by dots 90 in FIG. 4. This angle is known as the polarizing angle or Brewster's angle.

Brewster's Law may be derived empirically by observing that, at this polarizing angle, the sum of the angle of incidence of signal 76 with respect to normal 72 and the angle of refraction of signal 86 with respect to normal 72 equal ninety degrees (90°). That is:

$$\theta_1 + \theta_3 = 90°$$

From Snell's Law, above:

$$n_1 \sin \theta_1 = n_2 \sin \theta_3$$

Combining these two equations yields:

$$n_1 \sin \theta_1 = n_2 \sin(90° - \theta_1) = n_2 \cos \theta_1$$

Which yields Brewster's Law:

$$\tan \theta_1 = n_2/n_1.$$

For air, $n_1$ is approximately equal to 1.00 yielding:

$$\tan \theta_1 = n_2.$$

The polarizing angle or Brewster's angle ($\theta_1$) can thus be determined:

$$\theta_1 = \tan^{-1} n_2$$

Figure 5:
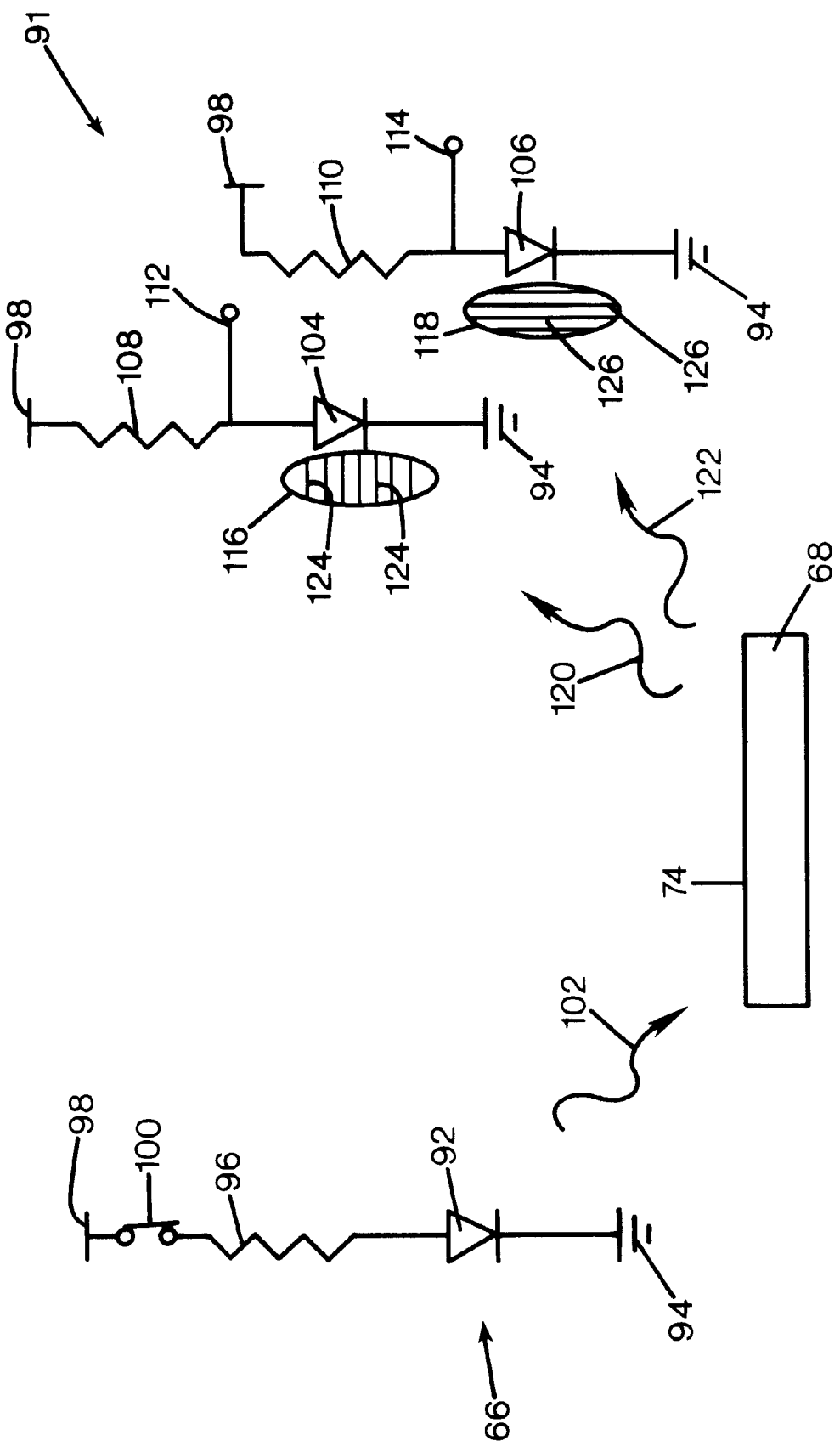
FIG. 5 is a diagram of the operation of the media detector shown in FIGS. 1–3 in accordance with the present invention.

A diagram 91 of an embodiment of media detector 46 constructed in accordance with the present invention that utilizes Brewster's Law to differentiate between glossy-finish and matte-finish print media is shown FIG. 5. In FIG. 5, sheet 68 of print media is shown, as is surface 74 thereof. Also shown is source 66 which is represented by a diode 92, the cathode of which is connected to ground 94 and the anode of which is connected to a current limiting resistor 96 that is connected to a power source 98 via a switch 100. Diode 92 emits an unpolarized incident first light signal 102 on surface 74 of print media sheet 68, as shown.

As can be seen in FIG. 5, media detector 46 includes a pair of photo diodes 104 and 106 that act as reflected light sensors. The cathodes of photo diodes 104 and 106 are each connected to ground 94. The anode of diode 104 is connected to current limiting resistor 108 which is connected to power source 98 and the anode of diode 106 is connected to current limiting resistor 110 which is also connected to power source 98. Outputs 112 and 114 are electrically coupled to controller 30 of printing device 10 to transmit signals thereto, as more fully discussed below.

As can be further seen FIG. 5, media detector 46 further includes a pair of polarized filters 116 and 118 that are positioned between respective photo diodes 104 and 106 and print media sheet 68. Reflected light signals 120 and 122 are reflected from surface 74 of print media sheet 68 in response to first light signal 102. As can be seen FIG. 5, the polarization of polarized filter 116, represented by lines 124, is oriented to be at substantially a right angle to the polarization of polarized filter 118, which is represented by lines 126. It should be noted that the use of the word substantially in this document is used to account for things such as engineering and manufacturing tolerances, as well as variations not affecting performance of the present invention.

Light emitting diode 92 is positioned in housing 58 or, alternatively, somewhere else in printing device 10, so that unpolarized light signal 102 strikes surface 74 of sheet of print media 68 substantially at the above-described polarizing angle (i.e., Brewster's angle). Sheets of print media 68 having a matte-finish surface 74 disperse unpolarized light signal 102 so that reflected signals 120 and 122 are unpolarized. Unpolarized reflected signals 120 and 122 pass through polarized filters 116 and 118 and are partially attenuated by substantially the same amount so that photo diodes 104 and 106 sense the same signal strengths and begin to conduct current toward ground. This resulting current flow causes an equal voltage drop across current limiting resistors 108 and 110 which have substantially equal values.

Figure 6:
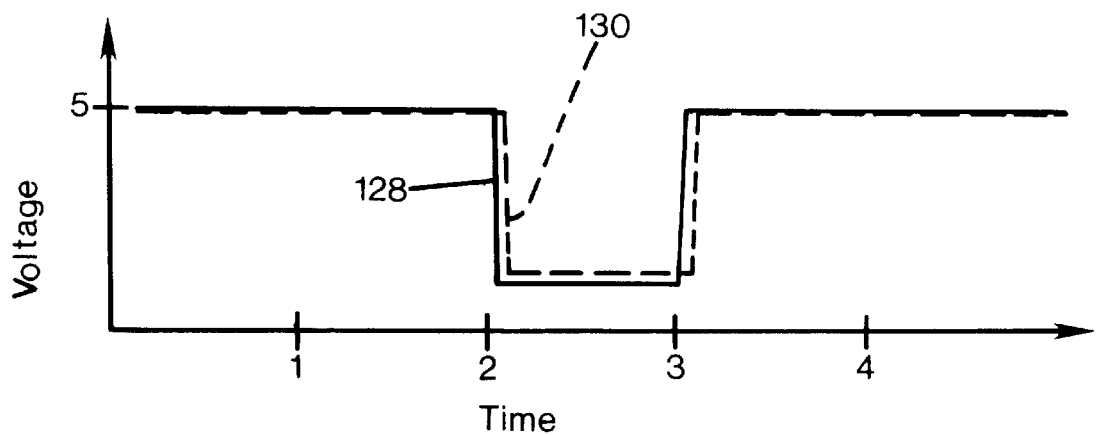
FIG. 6 is a diagram of output waveforms of the embodiment of the media detector shown in FIGS. 1–3 and 5 for matte-finish print media.

FIG. 6, is diagram of voltage waveforms at outputs 112 and 114. For a power source 98 of 5 volts, voltage signal 128 represents the output voltage at output 112 as a function of time with LED 92 of media detector 46 on between time two (2) milliseconds and three (3) milliseconds. Voltage signal 130 includes the voltage at output 114 as a function of time at output 114 with LED 92 of media detector 46 on between time two (2) milliseconds and three (3) milliseconds. As can be seen FIG. 6, signals 128 and 130 are substantially identical in magnitude or intensity, as well as shape, and thereby indicate to controller 30 that a sheet of print media 68 having a matte-finish surface 74 is entering print zone 16 of printer 10. Upon recognizing this, controller 30 adjusts printing device 10 to help optimize printing on this print media surface finish.

As discussed above in connection with FIG. 4, because unpolarized light signal 102 is optimized to strike surface 74 of print media sheet 68 substantially at a polarizing angle, if surface 74 of print media sheet 68 has a glossy-finish, reflected signals 120 and 122 will be polarized such that the polarized components are substantially perpendicular to the plane of incidence defined by the plane of FIG. 5. As can be seen FIG. 5, polarized filter 116 is oriented in media detector 46 such that the lines of polarization 124 are substantially orthogonal or perpendicular to the plane of incidence defined by the plane of FIG. 5. As can also be seen in FIG. 5, polarized filter 118 is oriented so that the lines of polarization 126 are substantially parallel to this plane. The orientation of filter 116 causes polarized signal 120 to pass therethrough and be only partially attenuated, reaching photo diode 104 and causing it to conduct current toward ground 94. This current flow causes a voltage drop across current limiting resistor 108 which can be sensed at output 112, as discussed above.

Figure 7:
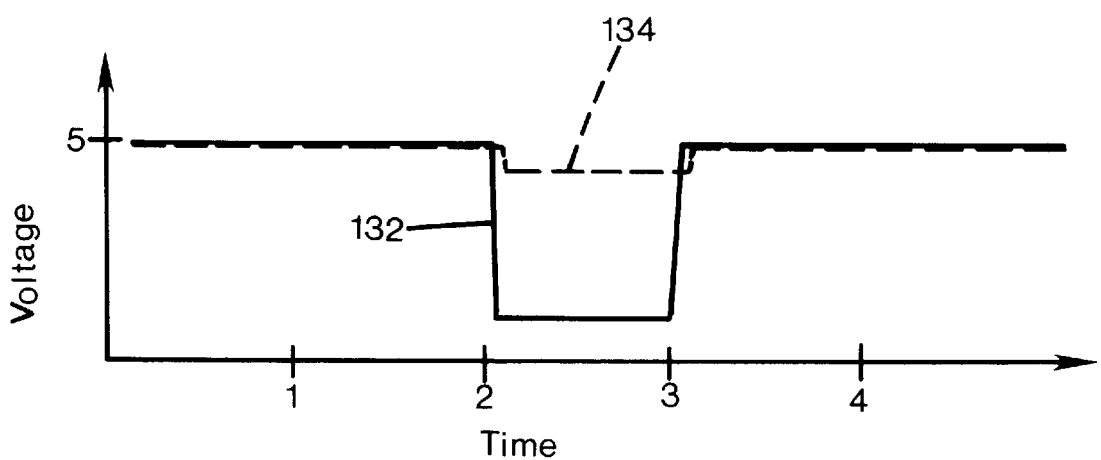
FIG. 7 is a diagram of output waveforms of the embodiment of the media detector shown in FIGS. 1–3 and 5 for glossy-finish print media.

A voltage versus time signal 132 at output 112 resulting from polarized reflected light signal 120 is shown in FIG. 7 with LED 92 of media detector 46 on between time two (2) and three (3) milliseconds. As can be seen FIG. 7, voltage signal 132 is substantially identical to voltage signals 128 and 130. Polarized filter 118 is oriented substantially orthogonal or perpendicular to the polarization of polarized reflected light signal 122 so that signal 122 is substantially totally attenuated. This attenuation causes a relatively lower strength reflected light signal to reach photo diode 106. This results in less current being conducted through current limiting resistor 110 and photo diode 106 to ground. Therefore, a lower voltage drop across current limiting resistor 110 occurs, as measured at output 114.

A signal 134 is shown in FIG. 7 which represents the voltage versus time measured at output 114. As can be seen in FIG. 7, signal 134 is different than signals 128, 130, and 132, being of a higher magnitude or intensity between time two (2) milliseconds and three (3) milliseconds when LED 92 of media detector 46 is on. Controller 30 is configured to recognize this difference between signals 132 and 134 as indicating the presence of a glossy-finish for surface 74 of print media sheet 68. Upon recognizing this difference, controller 30 adjusts printing device 10 for printing on this different print media surface finish.

Although the invention has been described and illustrated in detail, it is to be clearly understood that the same is intended by way of illustration and example only, and is not to be taken necessarily, unless otherwise stated, as an express limitation. For example, an alternative embodiment of the present invention utilizes only a single sensor and polarized filter to detect reflected light signals. In this embodiment, the polarized filter is positioned between a photo diode and sheet of print media, and oriented so that the lines of polarization of the filter are substantially orthogonal or perpendicular to the polarization of reflected polarized light signals. With this arrangement, the voltage drop across a current limiting resistor connected between the photo diode and power source is less for reflected polarized light signals due to substantially total attenuation when passing through the filter than for reflected unpolarized light signals which are only partially attenuated. As another example, in alternative embodiments of the present invention, the media detector of the present invention may be positioned other than within lower print media guide 48, such as on carriage 34 of printing device 10. In such embodiments, a test patch of glossy-finish print media may be scanned by the media detector and the reflected light signal stored in memory. The media detector then looks for this same reflected light signal during "picking" of sheets of print media by the printing device. If the media detector receives this reflected signal during illumination of a sheet of print media, then the sheet of print media is treated as having a glossy-finish. If not, then the sheet of print media is treated as having a matte-finish. As a further example, the current limiting resistors of alternative embodiments of the present invention may have different values. The spirit and scope of the present invention are to be limited only by the terms of the following claims.

What is claimed is:

1. A media detector for use in a printing device, comprising:
    a source that transmits an unpolarized first light signal, the source being positioned in the printing device so that the first light signal is transmitted toward a sheet of print media in the printing device at a selected first angle with respect to a normal to a surface of the sheet of print media;
    a sensor positioned in the printing device to detect an intensity of a reflected light signal from the sheet of print media, the sensor configured to produce a signal related to the intensity of the reflected light signal;
    wherein the reflected light signal is polarized for glossy-finish print media and unpolarized for matte-finish print media as a result of the selected first angle;
    a polarized filter positioned between the sensor and the sheet of print media so that the intensity of the reflected light signal detected by the sensor is less for a polarized reflected light signal than for an unpolarized reflected light signal; and
    a controller coupled to the sensor to receive the signal from the sensor, the controller configured to adjust the printing device for printing on glossy-finish print media or matte-finish print media based on the signal from the sensor.

2. The media detector of claim 1, wherein the first angle is selected such that the reflected light signal is polarized in a plane substantially orthogonal to a polarization of the polarized filter.

3. The media detector of claim 1, further comprising:
    a second sensor positioned in the printing device to detect the intensity of the reflected light signal from the sheet of print media, the second sensor configured to produce a second signal related to the intensity of the reflected light signal; and
    a second polarized filter positioned between the second sensor and the sheet of print media, and oriented so that the polarization of the second polarized filter is substantially parallel to a polarization of the reflected light signal;
    wherein the controller is also coupled to the second sensor to receive the second signal from the second sensor; and
    further wherein the controller is configured to adjust the printing device for printing on glossy-finish print media or matte-finish print media based on the second signal from the second sensor.

4. The media detector of claim 1, wherein the first angle is selected to be substantially equal to a Brewster's angle.

5. A media detector for use in a printing device, comprising:
    means for producing an unpolarized first light signal;
    means for detecting a reflected light signal from a sheet of print media in response to the first light signal;
    means for sensing polarization of the reflected light signal from the sheet of print media in response to the first light signal;
    means for differentiating between a glossy-finish sheet of print media and a matte-finish sheet of print media based on polarization of the reflected light signal; and
    means for adjusting the printing device for printing on the glossy-finish sheet of print media or the matte-finish sheet of print media to help optimize printing by the printing device.

6. The media detector of claim 5, wherein the reflected light signal is polarized for glossy-finish print media and unpolarized for matte-finish print media.

7. The media detector of claim 5, wherein the means for detecting includes
    a sensor positioned in the printing device to detect an intensity of the reflected light signal from the sheet of print media; and
    further wherein the means for sensing includes a polarized filter positioned the sensor and the sheet of print media so that the intensity of the reflected light signal detected by the sensor is less for a polarized reflected light signal than for an unpolarized reflected light signal.

8. The media detector of claim 7, further comprising:
    a second sensor positioned in the printing device to detect the intensity of the reflected light signal from the sheet of print media; and
    a second polarized filter positioned the second sensor and the sheet of print media, and oriented so that the polarization of the second polarized filter is substantially parallel to the polarization of the reflected light signal.

9. A method of differentiating between glossy-finish and matte-finish print media for use in a printing device, the method comprising the steps of:
    transmitting an unpolarized first light signal toward a sheet of print media at a first angle with respect to a normal to a surface of the sheet of print media;
    detecting an intensity of a reflected light signal from the sheet of print media; and
    differentiating between a polarized reflected light signal and an unpolarized reflected light signal to determine whether the sheet of print media has a glossy-finish or a matte-finish.

10. The method of claim 9, further comprising the step of selecting the first angle such that the reflected light signal is polarized in a plane substantially orthogonal to a plane including the normal.

11. The method of claim 10, wherein the first angle is selected to be substantially equal to a Brewster's angle.

12. The method of claim 9, further comprising the step of selecting the first angle to be substantially equal to a Brewster's angle.

13. The method of claim 9, further comprising the step of adjusting the printing device for printing on glossy-finish print media or matte-finish print media subsequent to the step of differentiating.

14. A printing device comprising the media detector as recited in claim 1.

15. A printing device comprising the media detector as recited in claim 5.

* * * * *